(12) United States Patent
Lupton et al.

(10) Patent No.: US 12,364,387 B2
(45) Date of Patent: Jul. 22, 2025

(54) ENDOSCOPE LIGHTING CONTROL WITH CAMERA EXTENSION

(71) Applicant: Cook Medical Technologies LLC, Bloomington, IN (US)

(72) Inventors: Jonathan K. Lupton, Thomasville, NC (US); Liam Breen, Ballina (IE); Vincent McHugo, Birdhill (IE); John C. Sigmon, Jr., Winston-Salem, NC (US); Christopher A. Carruthers, Winston-Salem, NC (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 105 days.

(21) Appl. No.: 18/340,209

(22) Filed: Jun. 23, 2023

(65) Prior Publication Data

US 2023/0414084 A1    Dec. 28, 2023

Related U.S. Application Data

(60) Provisional application No. 63/355,866, filed on Jun. 27, 2022.

(51) Int. Cl.
*A61B 1/06* (2006.01)
*A61B 1/005* (2006.01)
*A61B 1/045* (2006.01)
*A61B 1/05* (2006.01)

(52) U.S. Cl.
CPC ............... *A61B 1/05* (2013.01); *A61B 1/009* (2022.02); *A61B 1/045* (2013.01); *A61B 1/0655* (2022.02); *A61B 1/0684* (2013.01)

(58) Field of Classification Search
None
See application file for complete search history.

(56) References Cited

U.S. PATENT DOCUMENTS

| | | | |
|---|---|---|---|
| 7,918,783 B2 | 4/2011 | Maseda et al. |
| 8,007,440 B2 | 8/2011 | Magnin et al. |
| 8,190,238 B2 | 5/2012 | Moll et al. |
| 8,391,957 B2 | 3/2013 | Carlson et al. |
| 8,852,084 B2 | 10/2014 | Crank |
| 9,931,026 B2 | 4/2018 | Ha et al. |
| 10,478,052 B2 | 11/2019 | Konstorum et al. |
| 10,582,835 B2 | 3/2020 | Surti et al. |
| 10,582,837 B2 | 3/2020 | Hebert |
| 10,588,597 B2 | 3/2020 | Zhao et al. |

(Continued)

FOREIGN PATENT DOCUMENTS

EP    1284120 B1    2/2003

OTHER PUBLICATIONS

Partial European Search Report for Application No. 23181310.6 dated Nov. 9, 2023, 12 pages.

*Primary Examiner* — Christopher G Findley
(74) *Attorney, Agent, or Firm* — Vivacqua Crane, PLLC (57) ABSTRACT

A scope system is provided including an elongate tube, a movable member extending longitudinally at least partially within a lumen of the elongate tube, and a light on a distal portion of the elongate tube, the light configured to be controlled by proximal or distal movement of the movable member relative to the elongate tube along a longitudinal axis and/or rotational movement of the movable member about the longitudinal axis.

20 Claims, 6 Drawing Sheets

(56) References Cited

U.S. PATENT DOCUMENTS

| | | |
|---|---|---|
| 2006/0149129 A1* | 7/2006 | Watts ................ A61M 25/0152 |
| | | 600/113 |
| 2007/0244356 A1 | 10/2007 | Carrillo, Jr. et al. |
| 2013/0096376 A1 | 4/2013 | Takei et al. |
| 2017/0238962 A1 | 8/2017 | Hansen et al. |
| 2017/0251908 A1 | 9/2017 | Surti et al. |
| 2018/0110401 A1* | 4/2018 | Watanabe ............... A61B 5/061 |
| 2020/0022565 A1* | 1/2020 | Sigmon, Jr. ........ A61M 25/0067 |
| 2020/0163534 A1 | 5/2020 | Surti et al. |
| 2020/0323424 A1 | 10/2020 | Hazelton et al. |
| 2021/0100627 A1 | 4/2021 | Soper et al. |

\* cited by examiner

ENDOSCOPE LIGHTING CONTROL WITH CAMERA EXTENSION

CROSS-REFERENCE TO RELATED APPLICATIONS

The present application claims the benefit of U.S. Provisional Patent Application No. 63/355,866, filed on Jun. 27, 2022, the entirety of which is incorporated herein by reference for all purposes.

FIELD

The present disclosure relates to medical devices. More particularly, the disclosure relates to controlling the lighting of the camera extension of endoscope systems.

BACKGROUND

The statements in this section merely provide background information related to the present disclosure and may not constitute prior art.

Internal body cavities and body lumens may become blocked, or the walls surrounding them may develop growths. In some cases, removal of these blockages or growths, or other treatment thereof, may be necessary. Endoscopic or other minimally invasive techniques may be used to treat these situations.

One type of treatment includes the use of catheters or other endoscopic devices that are inserted into the body lumen or cavity and toward the area where treatment is desired. Insertion of the endoscope to the target area can allow for visualization of the target area and a determination of the desired procedure and the specific location of the area to be treated.

In general, endoscopes have been designed to be operated with the same fundamental mechanisms, and have not had transformational improvements. Endoscopes generally include a camera and a set of wheels that an operator, such as a physician, operates with a first hand (in some cases, the left hand) to control scope deflection, while the second (generally, right) hand switches between the insertion tube of the endoscope and the accessory channel in order to control scope and device advancement, respectively, through the anatomy of a patient.

When performing an Endoscopic Retrograde Cholangiopancreatography ("ERCP") procedure with a duodenoscope and cholangioscope, navigating to the duodenum and cannulating the papilla require varying degrees of lighting for the endoscope camera systems for large and small cavities, and/or distant and close anatomical features. Particularly, the large cavity of the stomach requires brighter lighting than in the smaller cavity of the duodenum or the even smaller cavity of the biliary duct. In addition to brightness, the direction and placement of the lighting elements on an endoscope play a critical role in the illumination of a patient's anatomy and the overall image quality of the endoscope during a procedure.

For the best image and illumination quality, lighting and image/pixel brightness must be actively adjusted within hardware, software, or both. Active brightness control requires that a camera system provide feedback to the hardware/software in order to be able to adjust image characteristics and lighting element brightness properly. In the absence of image feedback, the ability to adjust lighting element(s) is imprecise, because the ability to determine if a lighting adjustment is adequate or excessive is lacking.

In the case of specialized endoscopes, which may utilize a single camera element for both duodenoscopy and cholangioscopy with multiple lighting elements distributed across an endoscope, once the camera element loses the ability to accurately provide duodenum lighting feedback to the hardware/software due to extension within the biliary duct, the hardware/software may attempt to increase brightness of the lighting elements to compensate for the darker confines and smaller lighting elements of the biliary duct. The lighting elements may be in contact with a patient's tissue while at maximum brightness level, which may lead to thermal damage.

SUMMARY

In an example, the present disclosure provides a scope system. The scope system includes an elongate tube defining a longitudinal axis therethrough. The elongate tube includes a lumen extending therethrough and a distal surface including a light. The scope system further includes a movable member extending longitudinally at least partially within the lumen, the movable member including a second lumen extending therethrough. The scope system further includes a camera extending longitudinally at least partially within the second lumen, the light received by a lens of the camera. An illumination characteristic of the light is configured to be controlled by: proximal or distal movement of the movable member relative to the elongate member relative to the elongate tube along the longitudinal axis; rotational movement of the movable member about the longitudinal axis; or any combination of by proximal or distal movement of the movable member relative to the elongate tube along the longitudinal axis and rotational movement of the movable member about the longitudinal axis. An outer surface of the movable member and/or an inner surface of the elongate tube may include a conductive surface configured to provide an indication of proximal or distal and/or rotational movement of the movable member relative to the elongate tube. An outer surface of the movable member and/or an inner surface of the elongate tube may include a visual marker configured to provide an indication of proximal, distal, and/or rotational movement of the movable member relative to the elongate tube. An outer surface of the movable member and/or an inner surface of the elongate tube may include a protrusion, a depression, a keying feature, and/or a shape set curve configured to provide an indication of proximal, distal, and/or rotational movement of the movable member relative to the elongate tube. Each of a distal end of the movable member and the distal end of the elongate tube may be configured for independent steering, wherein a proximal end of the scope system may include switchable steering controls, and wherein the illumination characteristic of the light may be controllable by switching the switchable steering controls. The elongate tube and/or the movable member may include a motion sensor configured to detect an indication of proximal or distal and/or rotational movement of the movable member relative to the elongate tube. The elongate tube and/or the movable member may include a photosensor configured to detect an indication of the illumination characteristic surrounding the distal surface. The illumination characteristic of the light may be configured to be controlled by providing feedback from a motion sensor or a photosensor to a lighting control system. The scope system may be configured to provide a user with at least one of a haptic indication and a visual indication of the proximal or distal movement and/or the rotational movement of the movable member. The scope system may be configured for manual control of the illumination characteristic of the light.

In another example, the present disclosure provides a scope system. The scope system includes an elongate tube including a lumen extending therethrough and a distal end section. The scope system further includes an accessory channel movably disposed at least partially within the lumen of the elongate tube, the accessory channel including a second lumen extending therethrough. The scope system further includes a camera extending longitudinally at least partially within the second lumen, the camera including a lens. A distal section of the accessory channel is rotatably movable about a pivot point between a forward-facing direction and an angled direction, the pivot point being fixed relative to the distal end section of the elongate tube. A light is fixed to the distal section of the accessory channel such that when the distal section of the accessory channel rotates between the forward-facing direction and the angled direction, the light also rotates relative to the distal end section of the accessory channel, and the light received by the lens. An illumination characteristic of the light is configured to be at least partially controlled by at least one of a proximal movement of the elongate tube, a distal movement of the elongate tube, and a rotational movement of the distal section about the pivot point between the forward-facing direction and the angled direction. Each of the distal section of the accessory channel and the distal end section of the elongate tube may be configured for independent steering, wherein a proximal end of the scope system may include switchable steering controls, and wherein the light may be configured to be controlled by switching the switchable steering controls. The elongate tube and/or the accessory channel may include a motion sensor configured to detect an indication of rotational movement of the distal section about the pivot point and/or proximal or distal movement of the distal end section. The distal end section and/or the distal section may include a photosensor configured to detect an indication of the illumination characteristic surrounding the distal end section. The illumination characteristic of the light may be configured to be controlled by providing feedback from a motion sensor or a photosensor to a lighting control system. The scope system may be configured to provide a user with an indication of the proximal or distal movement of the distal end section and/or the rotational movement of the distal section of the accessory lumen about the pivot point. The scope system may be configured for manual control of the illumination characteristic of the light.

In yet another example, the present disclosure provides a scope system. The scope system includes an elongate tube defining a longitudinal axis therethrough. The elongate tube includes a lumen extending therethrough and a distal surface including a light. The scope system further includes a movable member extending longitudinally at least partially within the lumen, the movable member including a second lumen extending therethrough. The scope system further includes a photosensor on the elongate tube and/or the movable member configured to detect an indication of an illumination characteristic surrounding the distal surface and/or distal or proximal movement of the movable member relative to the elongate tube and/or rotational movement of the movable member about the longitudinal axis. The scope system further includes a detection circuit electronically connected to the photosensor, the detection circuit including a processor. The processor is configured to cause an increase in a level of the illumination characteristic when the photosensor detects an indication of an illumination characteristic that is lower than a predetermined minimum level of the illumination characteristic. The processor is configured to cause a decrease in a level of the illumination characteristic when the photosensor detects an indication of an illumination characteristic that is higher than a predetermined maximum level of the illumination characteristic. The scope system may further include a camera extending longitudinally at least partially within the second lumen, the camera including the photosensor. The elongate tube and/or the movable member may include a motion sensor configured to detect an indication of proximal, distal, or rotational movement of the movable member relative to the elongate tube.

Further areas of applicability will become apparent from the description provided herein. It should be understood that the description and specific examples are intended for purposes of illustration only and are not intended to limit the scope of the present disclosure.

DRAWINGS

In order that the present disclosure may be well understood, there will now be described various forms thereof, given by way of example, reference being made to the accompanying drawings. The components in the figures are not necessarily to scale. Moreover, in the figures, like-referenced numerals designate corresponding parts through the different views.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In adding reference denotations to elements of each drawing, although the same elements are displayed on a different drawing, it should be noted that the same elements have the same denotations. In addition, in describing one aspect of the present disclosure, if it is determined that a detailed description of related well-known configurations or functions blurs the gist of one aspect of the present disclosure, it will be omitted.

In the following discussion, the terms "proximal" and "distal" will be used to describe the opposing axial ends of the device, as well as the axial ends of various component features. The term "proximal" is used in its conventional sense to refer to the end of the device (or component) that is closest to the medical professional during use of the assembly. The term "distal" is used in its conventional sense to refer to the end of the device (or component) that is initially inserted into the patient, or that is closest to the patient during use. The term "longitudinal" will be used to refer to an axis that aligns with the proximal-distal axis of the device (or component). The terms "radially" and "radial" will be used to refer to elements, surfaces, or assemblies relative to one another that may extend perpendicularly from a longitudinal axis. The term "circumference," "circumferentially," and "circumferential" will be used to refer to elements, surfaces, or assemblies relative to one another encircling a longitudinal axis at a radius.

The uses of the terms "a" and "an" and "the" and similar referents in the context of describing the present disclosure (especially in the context of the following claims) are to be construed to cover both the singular and the plural, unless otherwise indicated herein or clearly contradicted by context. The use of the term "plurality of" is defined by the Applicant in the broadest sense, superseding any other implied definitions or limitations hereinbefore or hereinafter unless expressly asserted by Applicant to the contrary, to mean a quantity of more than one. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein the terms "comprise(s)," "include(s)," "having," "has," "can," "contain(s)," and variants thereof, are intended to be open-ended transitional phrases, terms, or words that do not preclude the possibility of additional acts or structures. The present description also contemplates other examples "comprising," "consisting of," and "consisting essentially of," the examples or elements presented herein, whether explicitly set forth or not.

In describing elements of the present disclosure, the terms $1^{st}$, $2^{nd}$, first, second, A, B, (a), (b), and the like may be used herein. These terms are only used to distinguish one element from another element, but do not limit the corresponding elements irrespective of the nature or order of the corresponding elements.

Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

As used herein, the term "about," when used in the context of a numerical value or range set forth means a variation of ±15%, or less, of the numerical value. For example, a value differing by ±15%, ±14%, ±10%, or ±5%, among others, would satisfy the definition of "about," unless more narrowly defined in particular instances.

Figure 1:
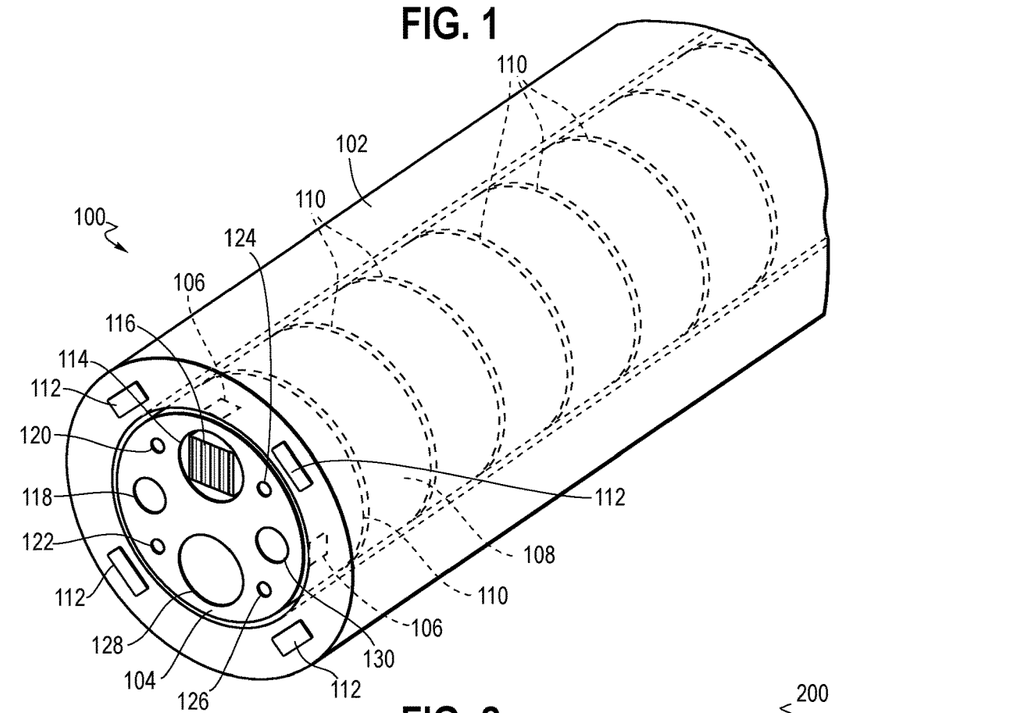
FIG. 1 illustrates a perspective view of a distal end of an example of a steerable endoscopic system including lighting elements and conductive rings, according to the principles of the present disclosure.

Referring to FIG. 1, a distal end of an example of a steerable endoscopic system 100 is illustrated. Steerable endoscopic system 100 includes a longitudinally-extending endoscope catheter 104 within a longitudinally extending lumen in catheter sleeve 102. Endoscope catheter 104 includes longitudinal deflection cable lumens 120, 122, 124, 126, camera lumen 114, and light-emitting diode lumen 118 each parallel to the longitudinal axis. Endoscope catheter 104 further includes additional longitudinal lumens 128, 130, each of which is parallel to the longitudinal axis and may be independently configured for suction, irrigation, insufflation, camera lens washing, and/or passing accessories or configured to house a suction device, an irrigation device, an insufflation device, a camera lens washing device, or a light-emitting diode, or to pass accessories. Camera lumen 114 is configured to house camera 116. Light-emitting diode lumen 118 may include a light-emitting diode, a light fiber, or other elements configured to provide illumination.

Endoscope catheter 104 includes an outer surface 108 that includes a conductive ring 110 or a plurality of conductive rings 110 circumferentially encircling outer surface 108 perpendicular to the longitudinal axis.

Catheter sleeve 102 includes a lighting element 112 or a plurality of lighting elements 112 in the distal end of catheter sleeve 102. Examples of lighting element 112 or plurality lighting elements 112 may include a light-emitting diode, a light fiber, or other elements configured to provide illumination.

In still other examples, endoscope catheter 104 and/or catheter sleeve 102 may pivot, rotate, and/or move in relation to each other and each in relation to other elements of steerable endoscopic system 100. Illumination of lighting elements on endoscope catheter 104 and/or catheter sleeve 102 and/or other sections or elements of steerable endoscopic system 100 may be configured to be controlled by movement of endoscope catheter 104 and/or catheter sleeve 102 relative to each other or each relative to other elements or sections of steerable endoscopic system 100. Alternatively, illumination of lighting elements on endoscope catheter 104 and/or catheter sleeve 102 and/or other sections or elements of steerable endoscopic system 100 may be configured to be controlled by a user controlling movement of endoscope catheter 104 and/or catheter sleeve 102 and/or other elements and/or sections of steerable endoscopic system 100.

Movement of endoscope catheter 104 and/or catheter sleeve 102 and/or other elements and/or sections of steerable endoscopic system 100 may be detected at or from the distal end of the steerable endoscopic system 100. For example, the inner surface of the distal end of catheter sleeve 102 includes a sensor 106 or a plurality of sensors 106 evenly distributed about the inner surface of the distal end of catheter sleeve 102. Examples of sensor 106 or plurality of sensors 106 may be electrical sensors, mechanical sensors, locating sensors, photosensors, illumination sensors, and motion sensors that may be capable of detecting movement and providing feedback to a lighting and camera control system located internally or externally to the steerable endoscope system 100. The feedback may be variable based on amount of movement or extension, or a toggle to indicate movement or extension of a static or adjustable length. Additionally, or alternatively, sensor 106 or plurality of sensors 106 may be analog or digital linear encoders. Additionally, or alternatively, sensor 106 or plurality of sensors 106 may be capable of detecting movement and/or providing feedback by optical, magnetic, inductive, capacitive, and/or eddy current technologies. The feedback provided to the lighting and camera control system may be used by the lighting and control system to independently adjust illumination brightness of lighting element 112 or plurality of lighting elements 112 and other sources of illumination of steerable endoscope system 100, or used to adjust other relevant characteristics configured to improve image and/or illumination quality and/or used to prevent unnecessary or excessive usage of lighting element 112 or plurality of lighting elements 112 and other sources of illumination of steerable endoscope system 100. Steerable endoscope system 100 may additionally include a user interface internal or external to steerable endoscope system 100 configured to manually override the lighting and camera control system and/or manually adjust lighting illumination by user manipulation of device sections, buttons, or other features. Alternatively, lighting may be controlled by electrical connections or interactions between sensors and active and/or passive control electronics.

In other examples, movement of endoscope catheter 104 and/or catheter sleeve 102 and/or other elements and/or sections of steerable endoscope system 100 may be detected within or from the middle portion or the central portion of steerable endoscopic system 100. Alternatively, movement of endoscope catheter 104 and/or catheter sleeve 102 and/or other elements and/or sections of steerable endoscope system 100 may be detected within or from the proximal end or handle of steerable endoscopic system 100.

Additionally, or alternatively, the inner surface of catheter sleeve 102 may include additional sensors 106 proximal to distal end of catheter sleeve 102. The movement of endoscope catheter 104 proximally or distally relative to catheter sleeve 102 such that a conductive ring 110 confronts or approximates sensor 106 or plurality of sensors 106 and sensor 106 or plurality of sensors 106 may be configured to detect an indication of movement of endoscope catheter 104 proximally or distally relative to catheter sleeve 102. In addition, or alternatively, endoscope catheter 104 may move rotationally relative to the inner surface of catheter sleeve 102 such that sensor 106 or plurality of sensors 106 may be configured to detect an indication of rotational movement of endoscope catheter 104 relative to catheter sleeve 102. Sensor 106 or plurality of sensors 106 may include photosensors configured to detect an illumination characteristic in the vicinity of the distal end of steerable endoscopic system 100. Examples of illumination characteristics may include an illumination level, an illumination color, an illumination frequency, gain, contrast, and exposure. Detection of an indication of movement of endoscope catheter 104 relative to catheter sleeve 102 may provide feedback to the lighting and camera control system to adjust illumination brightness of lighting element 112 or plurality of lighting elements 112 and other sources of illumination of steerable endoscope system 100, or to adjust other relevant characteristics configured to improve image and/or illumination quality and/or signal processing and/or used to prevent unnecessary or excessive usage of lighting element 112 or plurality of lighting elements 112 and other sources of illumination of steerable endoscope system 100. An outer surface of catheter sleeve 102 may include a sensor or a plurality of sensors configured to detect movement of the catheter sleeve relative to other components of steerable endoscopic system 100.

Figure 2:
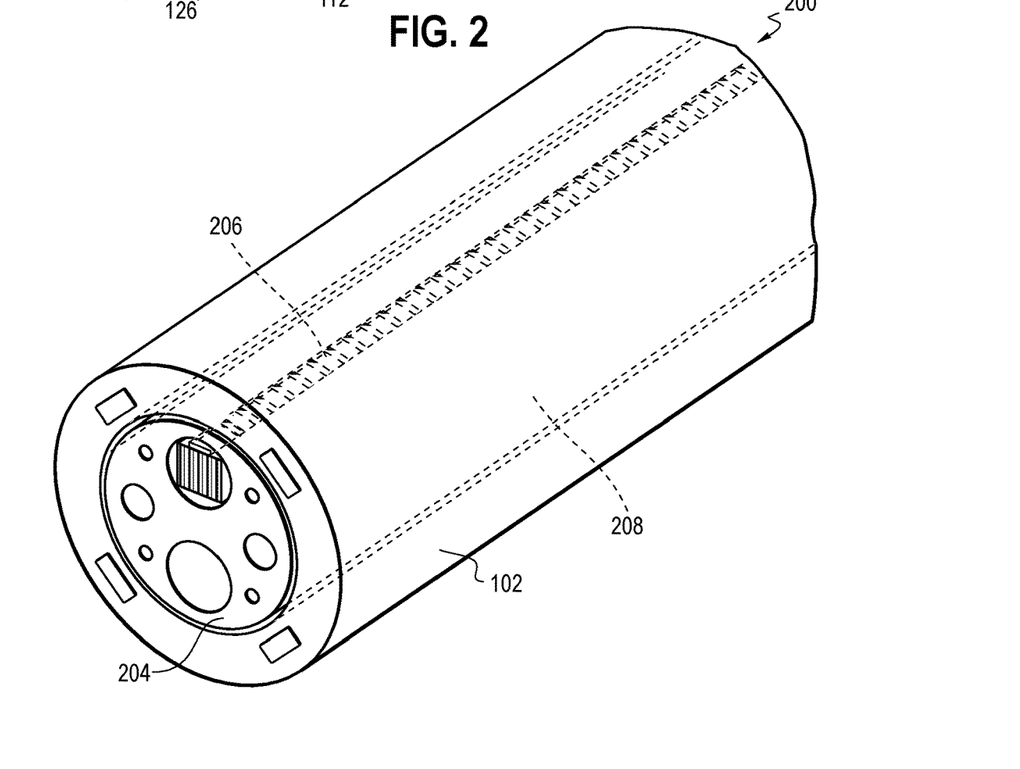
FIG. 2 illustrates a perspective view of a distal end of another example of a steerable endoscopic system including lighting elements and a conductive strip, according to the principles of the present disclosure.

Referring to FIG. 2, another example of a steerable endoscope system 200 includes catheter sleeve 102 and endoscope catheter 204. Endoscope catheter 204 includes outer surface 208 including conductive strip 206 along outer surface 208 parallel to the longitudinal axis of steerable endoscope system 200. Outer surface 208 may include a plurality of conductive strips 206 along outer surface 208 parallel to the longitudinal axis of steerable endoscope system 200 and evenly spaced apart about the circumference of outer surface 208. The movement of endoscope catheter 204 proximally or distally relative to catheter sleeve 102 such that a conductive strip 206 confronts or approximates sensor 106 or plurality of sensors 106 and sensor 106 or plurality of sensors 106 may detect an indication of movement of endoscope catheter 204 proximally or distally relative to catheter sleeve 102. In addition, or alternatively, endoscope catheter 204 may move rotationally relative to the inner surface of catheter sleeve 102 such that sensor 106 or plurality of sensors 106 may detect an indication of rotational movement of endoscope catheter 204 relative to catheter sleeve 102.

In other examples, an endoscope catheter may include a conductive surface, such as conductive rings, strips, and/or pads (or other conductive components/surfaces) on the outer surface of the endoscope catheter along the full length or a partial length of the endoscope catheter configured to provide an indication of proximal, distal, and/or rotational movement of the endoscope catheter relative to the catheter sleeve. In still other examples, an endoscope catheter may include a plurality of sensors on the outer surface of the endoscope catheter along the full length or a partial length of the endoscope catheter configured to detect an indication of proximal, distal, and/or rotational movement of the endoscope catheter relative to the catheter sleeve and/or configured to detect an indication of illumination level of the environment around the distal end of the steerable endoscopic system. In still other examples, an inner surface of a catheter sleeve may include conductive rings, strips, and/or pads on the inner surface of the catheter sleeve along the full length or a partial length of the catheter sleeve configured to provide an indication of proximal, distal, and/or rotational movement of the catheter sleeve relative to the endoscope catheter. In still other examples, an inner surface of a catheter sleeve may include a plurality of sensors on the inner surface of the catheter sleeve along the full length or a partial length of the catheter sleeve configured to detect an indication of proximal, distal, and/or rotational movement of the endoscope catheter relative to the catheter sleeve and/or other elements of the steerable endoscope system. In still other examples, the inner surface and the outer surface of the catheter sleeve may include a plurality of sensors along the full length or a partial length of the catheter sleeve configured to detect an indication of proximal, distal, and/or rotational movement of the endoscope catheter relative to the catheter sleeve, and/or the catheter sleeve relative to the endoscope catheter and/or other elements of the steerable endoscopic system, and/or the endoscope catheter and the catheter sleeve relative to each other and/or each of the endoscope catheter and the catheter sleeve relative to other elements of the steerable endoscopic system. The outer surface of the catheter sleeve may additionally include a sensor or a plurality of sensors configured to detect an indication of illumination level of the environment around the distal end of the steerable endoscopic system. Examples of an indication may include a visual indication and a haptic indication.

In still other examples, an endoscope catheter may include visual features or visual markers including, but not limited to, lines, text, dots, and/or colors along the full length or a partial length of the outer surface of the endoscope catheter that may be configured to provide an indication of proximal, distal, and/or rotational movement of the endoscope catheter relative to the catheter sleeve. In still other examples, an endoscope catheter may include mechanical features, including, but not limited to, raised surfaces, depressions, keying features, shape set curves, and/or attachments along the full length or a partial length of the outer surface of the endoscope catheter that may be configured to provide an indication of proximal, distal, and/or rotational movement of the endoscope catheter relative to the catheter sleeve. In still other examples, a catheter sleeve may include visual features including, but not limited to, lines, text, dots, and/or colors along the full length or a partial length of the inner surface that may be configured to provide an indication of proximal, distal, and/or rotational movement of the catheter sleeve relative to the endoscope catheter. In still other examples, a catheter sleeve may include mechanical features, including, but not limited to, raised surfaces, depressions, keying features, shape set curves, and/or attachments along the full length or a partial length of the inner surface that may be configured to provide an indication of proximal, distal, and/or rotational movement of the catheter sleeve relative to the endoscope catheter.

In still other examples, a steerable endoscopic system may include mechanical or electrical components or features not integrated into either the endoscope catheter or the catheter sleeve and configured to detect distal, proximal, and/or rotational movement of the endoscope catheter relative to the catheter sleeve.

In still other examples, a steerable endoscope system may include independent steering of the endoscope catheter and/or the catheter sleeve at the distal end of the steerable endoscope system and switchable steering controls at the proximal end of the steerable endoscope system. The steerable endoscope system may include lighting elements configured to be controlled based on switching of the switchable steering controls. In certain examples, the endoscope catheter and/or the catheter sleeve may include additional mechanical supporting elements. In other examples, lighting may be configured to be controlled by electrical connections or interactions between sensors and active and/or passive control electronics.

In still other examples, the sensors or plurality of sensors may detect an indication of movement, amount of movement, camera catheter extension, amount of camera catheter extension, illumination, and/or amount of illumination and communicate the indication(s) to a user of the steerable endoscope system.

In still other examples, a handle of the steerable endoscopic system, or another section or portion of the steerable endoscopic system, may include one or more buttons, wheels, levers, switches, or other manual control elements configured to control illumination level of lighting elements of the steerable endoscopic system manually by a user. In still other examples, an external vision and lighting control and feedback system may include one or more buttons, wheels, levers, switches, or other manual control elements configured to control illumination level of lighting elements of the steerable endoscopic system manually by a user.

In still other examples, illumination levels may be detected other than by a camera in the camera lumen of the endoscope catheter. The catheter sleeve or other supporting mechanics of the distal portion of the steerable endoscopic system may include one or more additional cameras, illumination sensors, or other light detection elements.

Figure 3:
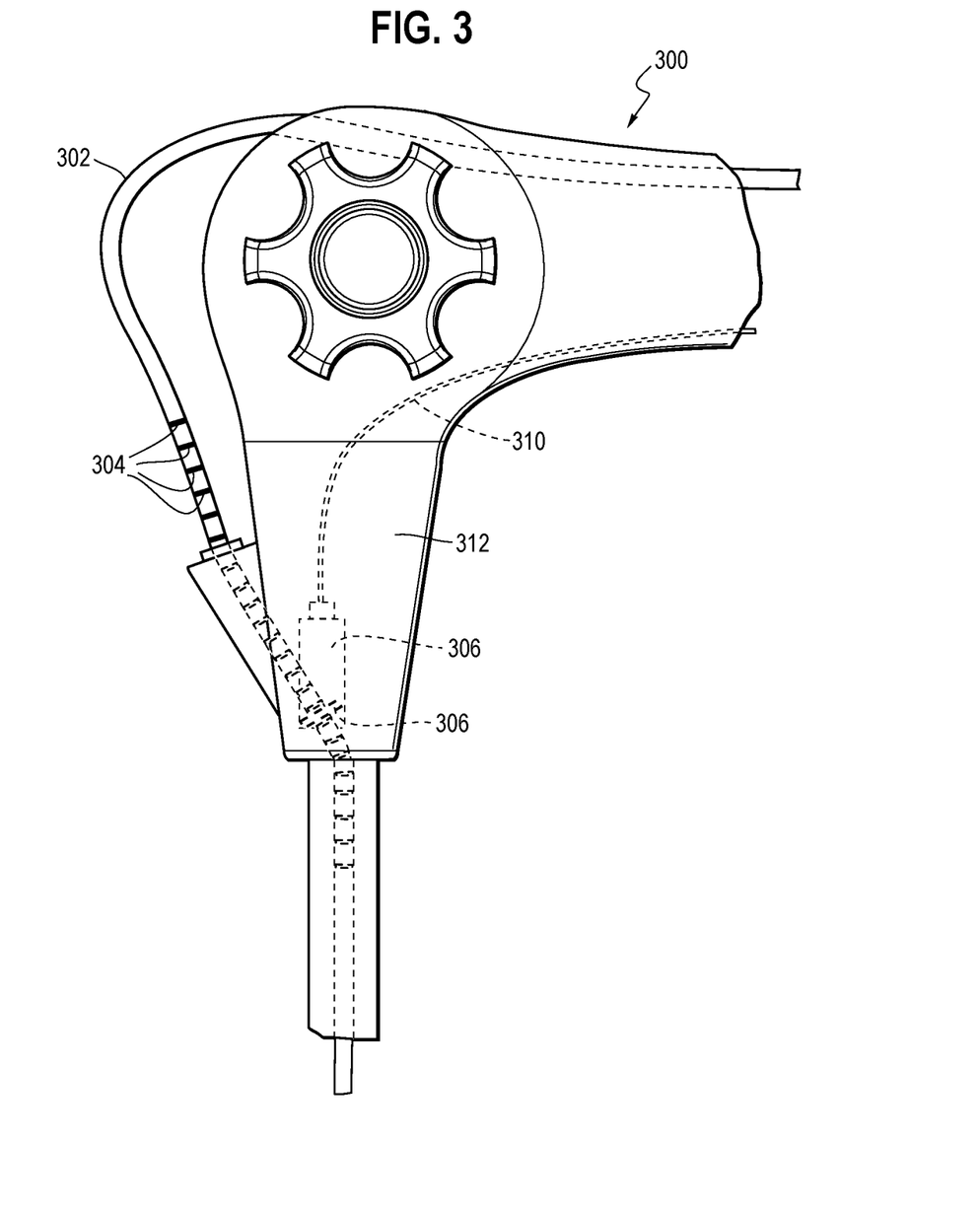
FIG. 3 illustrates a side view of an example of a handle of a steerable endoscope system including an example of an endoscope catheter including conductive rings at the handle, according to the principles of the present disclosure.

Referring to FIG. 3, a side view of an example of a handle 300 of a steerable endoscope system illustrated, including an example of an endoscope catheter 302. Endoscope catheter 302 includes a plurality of conductive rings 304 circumferentially encircling endoscope catheter 302 and evenly spaced apart. The proximal end of the endoscope catheter 302 is within handle base 312 and proximal and distal movement of endoscope catheter 302 is detected by detection circuit 306 within handle base 312. Detection circuit 306 may include a sensor or a plurality of sensors that may be configured to detect an indication of proximal or distal movement of plurality of conductive rings 304 relative to detection circuit 306, or a conductive element configured to interact with plurality of conductive rings 304 of endoscope catheter 302 to provide an indication of proximal or distal movement of plurality of conductive rings 304 relative to detection circuit. Detection circuit 306 may interact with an external vision and/or lighting control system by wire 310 within handle 300, by which a user may manually adjust illumination level of lighting elements and/or may be provided with an indication of the extent of proximal and distal endoscope catheter 302 extension. Detection circuit 306 may include a processor configured to detect an indication of movement and/or illumination level and adjust the illumination level of lighting element 112 or plurality of lighting elements 112 upward or downward.

A processor in detection circuit 306 may be in communication with a memory (not shown). In an example, a processor may also be in communication with additional elements, such as a display (not shown) and/or other processors. Examples of a processor may include a controller, a general processor, a central processor, a central processing unit, a microcontroller, a proportional-integral-derivative ("PID") controller, a server, an application specific integrated circuit ("ASIC"), a digital signal processor, a field programmable gate array ("FPGA"), a digital circuit, and/or an analog circuit.

A processor in detection circuit 306 may be one or more devices operable to execute logic. The logic may include computer executable instructions or computer code embodied in the memory or in other memory that, when executed by the processor, may cause the processor to perform the features implemented by the logic. In some examples, the processor may be part of a feedback loop to control operation of the lights based upon detection of an indication of an illumination characteristic. The processor may cause a light or a plurality of lights to increase an illumination characteristic in response to detection by a photosensor of an illumination characteristic that is lower than a predetermined minimum level of the illumination characteristic and/or a predetermined proximal, distal, rotational, and/or pivoting movement, and/or may cause a light or a plurality of lights to decrease an illumination characteristic in response to detection by a photosensor of an illumination characteristic that is higher than a predetermined maximum level of the illumination characteristic and/or a predetermined proximal, distal, rotational, and/or pivoting movement. The processing capability of the processor may be distributed across multiple entities, such as among multiple processors and memories, optionally including multiple distributed processing systems.

Figure 4:
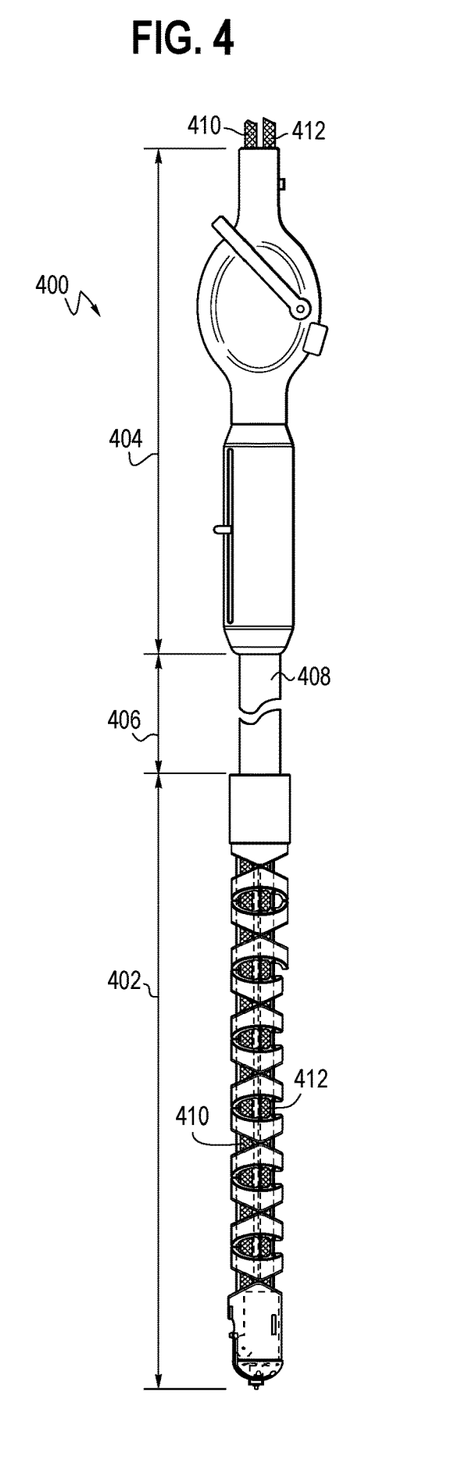
FIG. 4 illustrates a side view of yet another example of a steerable endoscopic system, according to the principles of the present disclosure.

Referring to FIG. 4, yet another example of an endoscope system 400 is illustrated. Endoscope system 400 may be generally shaped as an elongate tube including distal portion 402, central portion 406, and a proximal, or handle, portion 404. Central portion 406 may be a flexible, elongate tube, with at least one lumen 408 running throughout the length of central portion 406. Central portion 406 may connect distal portion 402 and handle portion 404 together. Lumen 408 of central portion 406 may extend through distal portion 402 and handle portion 404 of endoscope system 400 as well. Central portion 406 may be made of a braided material such as pebax with a polytetrafluoroethylene liner to provide sufficient torqueability and pushability. Other potential materials for central portion 406 include but are not limited to polyethylene, polypropylene, and nylon. Endoscope system 400 may further include two accessory channels 410, 412 each with a lumen running therethrough. First accessory channel 410 and second accessory channel 412 may be designed as individual elongated tubes that may be movable within lumen 408 of endoscope system 400, thus allowing longitudinal movement of first accessory channel 410 and second accessory channel 412 with respect to central portion 406. While the example of endoscope system 400 includes two accessory channels, first accessory channel 410 and second accessory channel 412, one or even three or more accessory channels may be used. For example, a single, larger accessory channel may be used to accommodate larger endoscopic tools. Further, in lieu of individual first accessory channel 410 and second accessory channel 412, a single elongate tube may be used with two or more lumens running through it. First accessory channel 410 and second accessory channel 412 may range in diameter anywhere from 1 to 10 millimeters. In certain examples, first accessory channel 410 may be 4.2 millimeters in diameter while second accessory channel 412 may be 3.7 millimeters in diameter. First accessory channel 410 and second accessory channel 412 may extend proximally from or past handle portion 404, through lumen 408 and into distal portion 402. Various tools, devices, and cameras may be inserted into and removed from first accessory channel 410 and second accessory channel 412.

Figure 5:
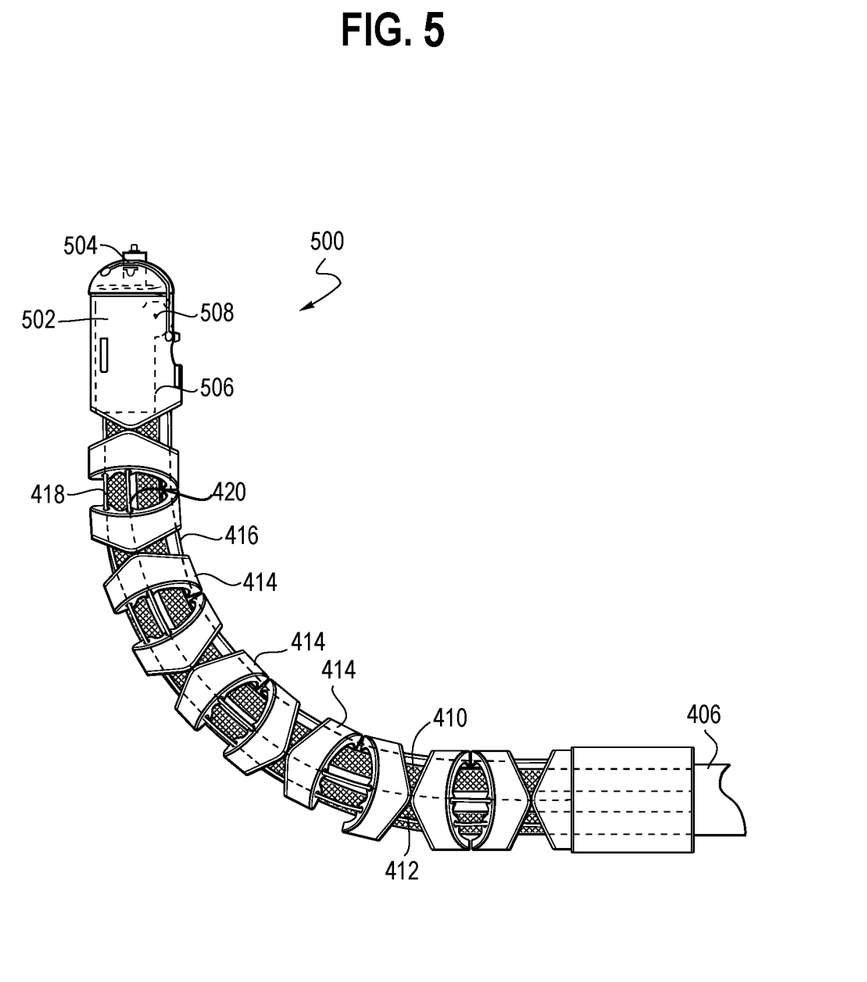
FIG. 5 illustrates a side view of an example of a distal portion of a steerable endoscopic system in a bent configuration, according to the principles of the present disclosure.

Referring to FIG. 5, a side view of an example of a distal portion 500 of a steerable endoscopic system in a bent configuration is illustrated. Distal portion 500 may have a flexible, rib-like construction with multiple individual ribs 414 connected together to create an elongate tube with a lumen. Ribs 414 may be made of a variety of materials, such as polycarbonate, nylon, polyethylene, polypropylene, and polyoxymethylene. First accessory channel 410 and second accessory channel 412 may extend through ribs 414 to distal end section 502 of distal portion 500.

Figure 6:
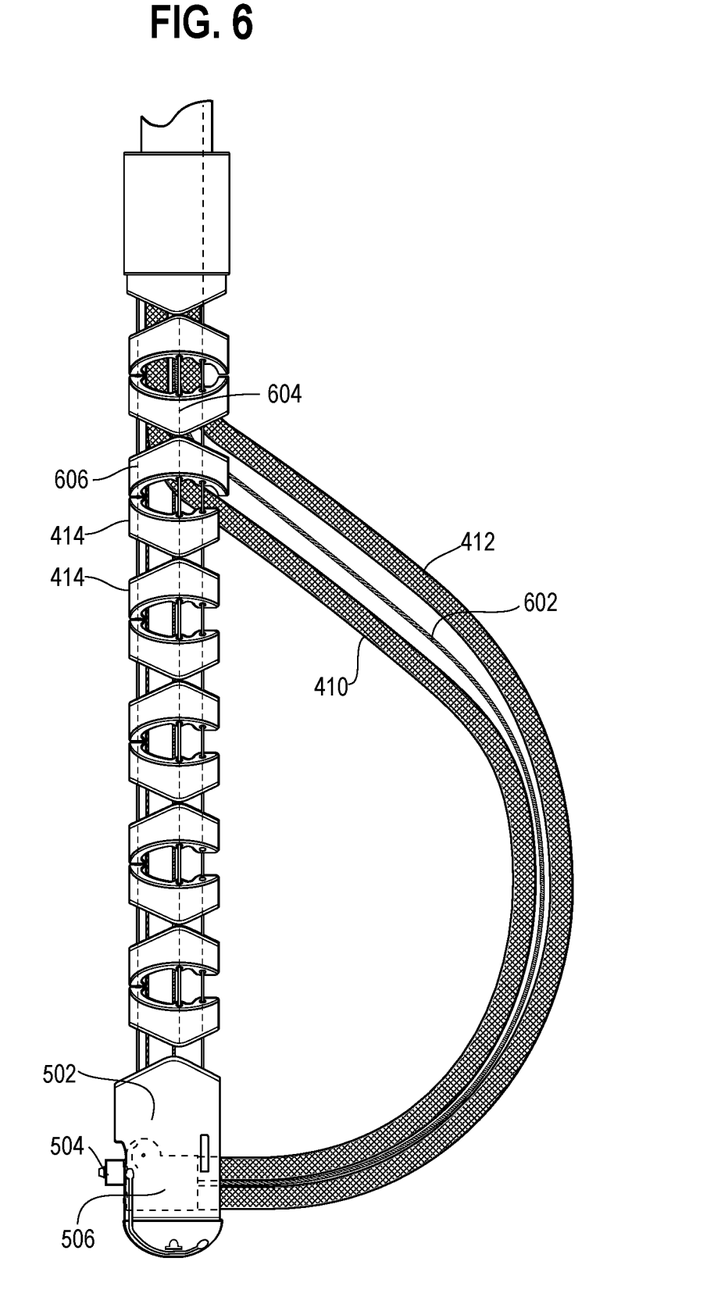
FIG. 6 illustrates a side view of another example of a distal portion of a steerable endoscopic system in a side-viewing configuration, according to the principles of the present disclosure.

Distal end section 502 may define a forward direction parallel to a longitudinal direction of distal end section 502. Distal end section 502 may include a pivot arm 506. Pivot arm 506 may be connected to distal end section 502 by pivot point support member 508. Pivot point support member 508 may create a pivot point, around which pivot arm 506 may rotate with respect to distal end section 502 to the position illustrated in FIG. 6. Pivot arm 506 may be moved between a forward-viewing configuration as illustrated in FIGS. 4 and 5, and a side-viewing configuration as illustrated in FIG. 6. In the forward-viewing configuration, the distal section of first accessory channel 410 and second accessory channel 412 substantially face in the forward direction. In the side-viewing configuration, the distal section of first accessory channel 410 and second accessory channel 412 substantially face a direction that is angled relative to the forward direction. A light-emitting diode ("LED") light 504 or a plurality of LED lights 504 is located on distal end section 502 to assist in navigation through a patient's GI tract. Alternatively, LED light 504 or plurality of LED lights 504 may be located at other locations on distal end section 502 such as pivot arm 506. LED light 504 or plurality of LED lights 504 may be distributed on, located on, or connected to pivot arm 506 and/or distal end section 502.

As illustrated in FIG. 6, the distal ends of first accessory channel 410 and second accessory channel 412 may be secured to pivot arm 506. Therefore, first accessory channel 410 and second accessory channel 412 may rotate with pivot arm 506 when moving pivot arm 506 between side-viewing and forward-viewing configurations. FIGS. 4 and 5 illustrate first accessory channel 410 and second accessory channel 412 in the forward-viewing configuration, while FIG. 6 illustrates first accessory channel 410 and second accessory channel 412 in the side-viewing configuration. As illustrated in FIG. 6, when in the side-viewing configuration and due to rotation of pivot arm 506, distal portions of first accessory channel 410 and second accessory channel 412 are bent outside of the confines of ribs 414 and then curve back towards and into pivot arm 506. Thus, in the forward-viewing configuration, the angle of curvature or bending radius of distal end section 502 is the same as the angle of curvature of first accessory channel 410 and second accessory channel 412 such that first accessory channel 410, second accessory channel 412, and distal end section 502 of endoscope system 400 are substantially parallel; but in the side-viewing configuration, the angle of curvature or bending radius of first accessory channel 410 and second accessory channel 412 is greater than the angle of curvature of distal end section 502 such that the distal portions of first accessory channel 410 and second accessory channel 412 extend outside the lumen of distal end section 502. To facilitate movement between the side-viewing and forward-viewing configurations, when viewed in cross-section, ribs 414 may have a U- or V-shaped design with an open section that allows first accessory channel 410 and second accessory channel 412 to move freely in and out of ribs 414.

To move pivot arm 506 from the forward-viewing configuration to the side-viewing configuration, first accessory channel 410 and second accessory channel 412 may be pushed in a distal direction relative to handle portion 404 and central portion 406, which applies a force through first accessory channel 410 and second accessory channel 412 to pivot arm 506. The resulting force causes pivot arm 506 to rotate about pivot point support member 508, thereby moving first accessory channel 410, second accessory channel 412, and pivot arm 506 into the side-viewing configuration. To move back to the forward-viewing configuration, a proximal force may be applied to first accessory channel 410 and second accessory channel 412 relative to handle portion 404 and central portion 406, thereby transferring the proximal force to pivot arm 506. The proximal force then causes pivot arm 506 to again rotate about pivot point support member 508 in the opposite direction, thereby moving first accessory channel 410, second accessory channel 412, and pivot arm 506 back to the forward-viewing configuration. To ensure that first accessory channel 410 and second accessory channel 412 move in unison during these movements, first accessory channel 410 and second accessory channel 412 may be secured together at any point along the length of endoscope system 400, or even along the entire length. In an example, first accessory channel 410 and second accessory channel 412 may be secured together using plastic tubing throughout the entire length of central portion 406. In another example, first accessory channel 410 and second accessory channel 412 may be secured together at the portions of first accessory channel 410 and second accessory channel 412 that extend outside the constraints of distal portion 402 when endoscope system 400 is in the side-viewing configuration. In further examples, a variety of other methods and structures may be used to assist in transitioning first accessory channel 410 and second accessory channel 412 between forward-viewing and side-viewing configurations. In other examples, rather than using single pivot arm 506, multiple pivot arms may be used, or a first pivot arm for first accessory channel 410 and a second pivot arm for second accessory channel 412. In still other examples, each of first accessory channel 410 and second accessory channel 412 may be moved between the forward-viewing and side-viewing configurations independently of each other. In still other examples, the degree of rotation of pivot arm 506 between the forward-viewing and side-viewing configurations may vary, potentially ranging from 45 degrees to greater than 135 degrees.

In addition to the ability to switch between forward-viewing and side-viewing configurations, distal portion 402 of endoscope system 400 may also bend and rotate as desired. FIG. 4 illustrates distal portion 402 in a straight configuration, while FIG. 5 illustrates distal portion 402 in a bent configuration. Endoscope system 400 may include a first drive member 416, a second drive member 418, and a third drive member 420. First drive member 416, second drive member 418, and third drive member 420 may extend through ribs 414. First drive member 416, second drive member 418, and third drive member 420 may be fixedly attached to distal end section 502 and extend through, or outside of the lumen to handle portion 404. First drive member 416 may be fixed on a wall of distal end section 502 while second drive member 418 and third drive member 420 may be fixed on opposing walls of distal end section 502. To move distal portion 402 from the straight configuration illustrated in FIG. 4 to the bend configuration illustrated in FIG. 5, first drive member 416 may be pulled in a proximal direction. The proximal movement of first drive member 416 may result in a force being applied through first drive member 416 and to distal end section 502. This force may cause the flexible, ribbed body of distal portion 402 to bend towards the configuration illustrated in FIG. 5. To move distal portion 402 back to a straight configuration, second drive member 418 and third drive member 420 may be pulled in a proximal direction. The proximal movement of second drive member 418 and third drive member 420 may result in a force being applied through second drive member 418 and third drive member 420 and to distal end section 502 that may move distal portion 402 back toward the straight configuration. In an example, distal portion 402 may include additional drive members fixedly attached to distal end section 502 and extend through or outside of the lumen to handle portion 404. First drive member 416, second drive member 418, and third drive member 420 may be drive mechanisms, deflection wires, or deflection cables.

First drive member 416, second drive member 418, and third drive member 420 may also secure individual ribs 414 of distal portion 402 together. First drive member 416, second drive member 418, and third drive member 420 may run through small holes in each individual rib 414, and sufficient tension may be applied to first drive member 416, second drive member 418, and third drive member 420 thereby securing ribs 414 together along first drive member 416, second drive member 418, and third drive member 420. Due to this design, ribs 414 may be shaped to allow for minimal contact between individual ribs 414. Each side of ribs 414 may be diamond-shaped when viewing endoscope system 400 from a side-view as illustrated in FIGS. 4-6. The diamond shape reduces the contact points between each rib 414, thus minimizing friction and allowing for easier bending of distal portion 402 to the bent configuration and maximum flexibility. Optionally, first drive member 416, second drive member 418, and/or third drive member 420 may also include built-in electrical wiring that allows first drive member 416, second drive member 418, and/or third drive member 420 to function as a circuit for LED light 504 or plurality of LED lights 504, to provide power to, or change illumination level of, LED light 504 or plurality of LED lights 504 following detection of an indication of illumination or an indication of proximal, distal, rotational, and/or pivoting movement of the endoscope catheter relative to the catheter sleeve, or proximal, distal, rotational, and/or pivoting movement of each of the endoscope catheter and catheter sleeve relative to other sections or elements of the endoscope system 400. In other examples, ribs 414 may be connected together using a variety of other methods, such as with mechanical hinges, adhesives, and other well-known devices. Further, additional elongate members may extend through ribs 414 similar to first drive member 416, second drive member 418, and third drive member 420 to provide additional support to distal portion 402.

Alternatively, or additionally, in certain examples, an electrical wire 606 may be secured adjacent to a drive member such as first drive member 416 or second drive member 418 or third drive member 420 such that electrical wire 606 may function as a circuit for LED light 504 or plurality of LED lights 504 to provide power to, or change illumination level of, LED light 504 or plurality of LED lights 504 following detection of an indication of illumination and/or an indication of proximal, distal, rotational, and/or pivoting movement of the endoscope catheter relative to the catheter sleeve, or proximal, distal, rotational, and/or pivoting movement of each of the endoscope catheter and catheter sleeve relative to other sections or elements of the endoscope system 400. Electrical wire 606 may be secured adjacent to a drive member by an additional tube, mechanical features, or other means of integration allowing free movement of wiring during articulation of first drive member 416, second drive member 418, and third drive member 420 and/or first accessory channel 410 and second accessory channel 412. In other examples, an electrical wire 604 may be secured adjacent to features of ribs 414 such that electrical wire 604 may function as a circuit for LED light 504 or plurality of LED lights 504 to provide power to, or change illumination level of, LED light 504 or plurality of LED lights 504 following detection of an indication of illumination and/or an indication of proximal, distal, rotational, and/or pivoting movement of the endoscope catheter relative to the catheter sleeve, or proximal, distal, rotational, and/or pivoting movement of each of the endoscope catheter and catheter sleeve relative to other sections or elements of endoscope system 400. Electrical wire 606 may be secured adjacent to ribs 414 via n additional tube, mechanical features, or other means of integration allowing free movement of wiring during articulation of first drive member 416, second drive member 418, and third drive member 420 to provide bending of distal portion 402 and/or first accessory channel 410 and second accessory channel 412. In still other examples, an electrical wire 602 may be secured adjacent to first accessory channel 410 and second accessory channel 412. First accessory channel 410, second accessory channel 412, and electrical wire 602 may be secured together at the portions of first accessory channel 410 and second accessory channel 412 that extend outside the constraints of distal portion 402 when endoscope system 400 is in the side-viewing configuration. Alternatively, first accessory channel 410, second accessory channel 412, and electrical wire 602 may be secured together using plastic tubing throughout the entire length of central portion 406. Alternatively, electrical wire 602 may be integrated into first accessory channel 410 and/or second accessory channel 412 via reinforcement coil wiring, dedicated wire lumens, or other means of integration. Alternatively, electrical wire 602 may be secured adjacent to first accessory channel 410 and/or second accessory channel 412 via an additional tube, mechanical features, or other means of integration allowing free movement of wiring during articulation of first drive member 416, second drive member 418, and third drive member 420 and/or first accessory channel 410 and second accessory channel 412. Alternatively, electrical wire 602 may be included within a separate tube with the lumen of the distal portion, providing for free movement of the wiring during distal articulation. Electrical wire 602 may function as a circuit for LED light 504 or plurality of LED lights 504 to provide power to, or change illumination level of, LED light 504 or plurality of LED lights 504 following detection of an indication of illumination and/or an indication of proximal, distal, rotational, and/or pivoting movement of the endoscope catheter relative to the catheter sleeve, or proximal, distal, rotational, and/or pivoting movement of each of the endoscope catheter and catheter sleeve relative to other sections or elements of endoscope system 400.

Examples of connections between a distal end section and a pivot arm may include direct wiring between the distal end section and the pivot arm, the pivot point support member being a conductive element, the pivot point support member including an internal cavity configured to allow wire connectivity between device sections, and/or additional mechanical conductors or conductive features on the distal end section and/or the pivot arm configured to maintain connectivity between the distal end section and the pivot arm during articulation.

Figure 7:
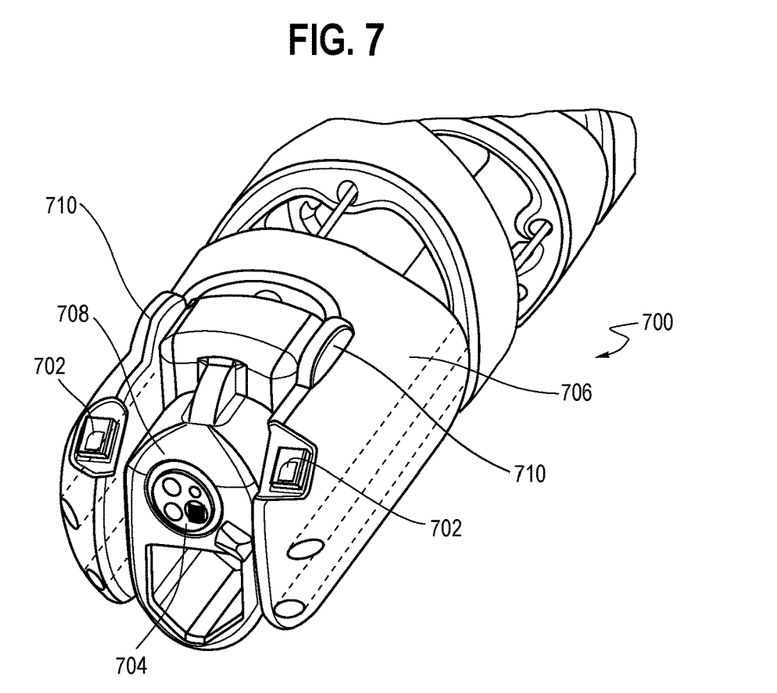
FIG. 7 illustrates a perspective view of a distal end of yet another example of a steerable endoscopic system including lights and a pivoting distal end portion, according to the principles of the present disclosure.

LED light 504 or plurality of LED lights 504 may be advantageously turned off when in cholangioscope mode so that only a camera catheter remains illuminated, so as to avoid a risk of burning a patient with LED light 504 or plurality of LED lights 504 while in the duodenum. LED light 504 or plurality of LED lights 504 may be turned off by a switch or mode selection knob in the handle of the steerable endoscope system that may respond to a detection of the position of distal portion 700 within a patient's anatomy. There may be a spare input/output line in a camera control system that may receive position and additional switch information, and the LED light 504 or plurality of LED lights 504 may be powered separately from lights 702 or a camera control system, thus providing for the camera control system to turn on and off LED light 504 or plurality of LED lights 504 as required depending on position or switch or mode selection knob setting.

Referring to FIG. 7, a perspective view of another example of distal portion 700 of a catheter sleeve of a steerable endoscopic system is illustrated, including lights 702 on a distal end section 706, and endoscope catheter 704 in a catheter sleeve including pivot arm 708. Endoscope catheter 704 may additionally include one or more lights on its distal end in one or more lumens of endoscope catheter 704, and also may include a camera in a lumen of endoscope catheter 704. Pivot point support members 710 may include conductive elements on the inside surface of distal end section 706 and/or the outside of pivot arm 708 configured to detect a position of pivot arm 708 relative to distal end section 706. Pivot point support member 710 may alternatively include an internal cavity configured to allow wire connectively or interaction of conductive elements on pivot arm 708 and distal end section 706 so as to maintain connective between distal end section 706 and pivot arm 708 during articulation. In addition to detecting an indication of proximal, distal, and/or rotational movement of endoscope catheter 704 relative to catheter sleeve, pivot arm 708 is configured to detect an indication of amount of rotation of pivot arm 708 relative to distal end section 706 between forward-viewing configuration and side-viewing configuration so as to provide feedback to a lighting and camera control system. Lighting element selection, usage, illumination level, and/or configuration may be adjusted based on feedback communicated to the lighting and camera control system from an indication of the amount of rotation of pivot arm 708 relative to distal end section detected by conductors or conductive features in distal end section 706, or detected by a distal portion, a central portion, or a proximal portion, or detected directly in the handle when steering is switched from distal end steering to cholangioscope steering.

Figure 8:
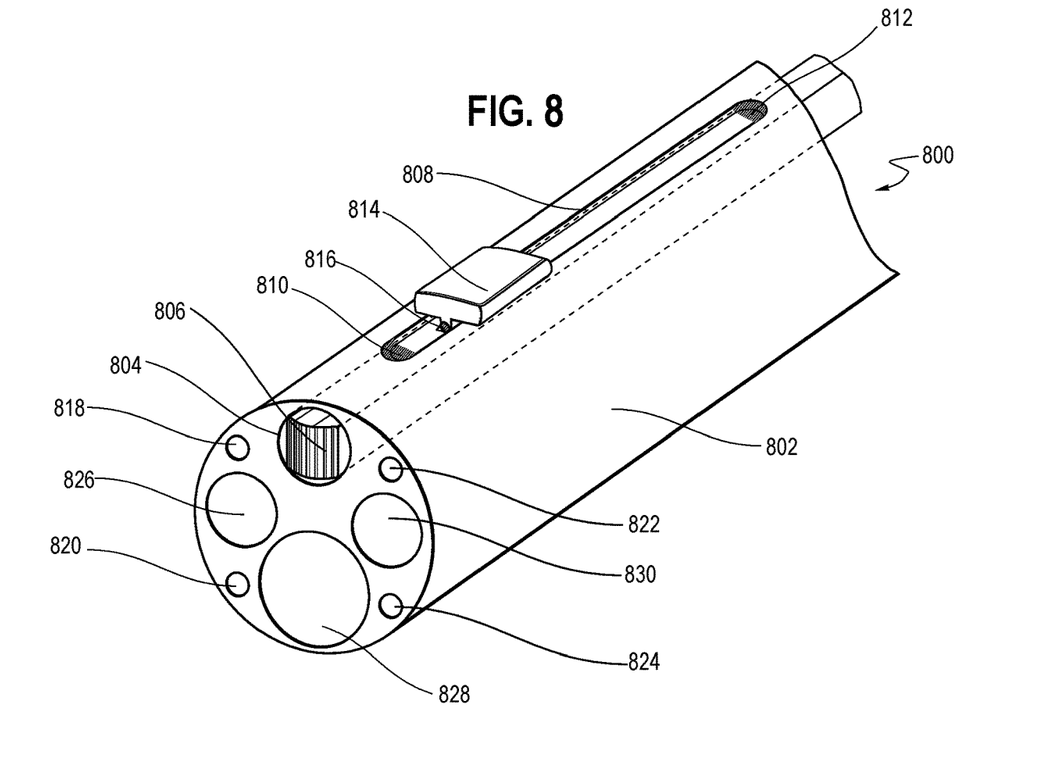
FIG. 8 illustrates a perspective view of a distal end of yet another example of a steerable endoscopic system including mechanical and electrical extension features, according to the principles of the present disclosure.

Referring to FIG. 8, a perspective view of a distal end of an endoscope catheter 800 is illustrated as the distal end resides within pivot arm 708. Endoscope catheter 800 includes longitudinal deflection cable lumens 818, 820, 822, 824, camera lumen 804, and light-emitting diode lumen 826, each of which is parallel to the longitudinal axis. Endoscope catheter 800 further includes additional longitudinal lumens 828 and 830, each of which is parallel to the longitudinal axis and may be independently configured for suction, irrigation, insufflation, camera lens washing, and/or passing accessories or configured to house a suction device, an irrigation device, an insufflation device, a camera lens washing device, or a light-emitting diode, or to pass accessories. Telescoping camera 806 may be housed in camera lumen 804 and may be advanced distally or retracted proximally through camera lumen 804 relative to pivot arm 708. Endoscope catheter 800 includes groove 808. Groove 808 is a recess in the outer surface of endoscope catheter 800 and extends longitudinally and proximally, parallel to the longitudinal axis of endoscope catheter 800, from a point proximal to the distal surface of endoscope catheter 800. Catheter sleeve 814 is shown as only a segment for purposes of illustration, to indicate the attachment of catheter sleeve 814 to groove 808. On both proximal and distal ends of the attachment of catheter sleeve 814 to groove 808 are conductors 816. Telescoping camera 806 may advance distally and retract proximally relative to pivot arm 708. At proximal and distal ends of groove 808 are proximal conductor 812 and distal conductor 810, respectively. Proximal conductor 812 and distal conductor 810 may interact with conductors 816 such that proximal movement of endoscope catheter 800 relative to catheter sleeve 814 may result in interaction of distal conductor 810 with conductor 816, thereby providing an indication of relative movement of endoscope catheter 800 and catheter sleeve 814 to a lighting and camera control system, and distal movement of endoscope catheter 800 relative to catheter sleeve 814 may result in interaction of proximal conductor 812 with conductor 816, thereby providing an indication of relative movement of endoscope catheter 800 and catheter sleeve 814 to a lighting and camera control system.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the disclosure may also relate, among others, to the following aspects:

A first aspect relates to a scope system, comprising: an elongate tube defining a longitudinal axis therethrough, the elongate tube comprising: a lumen extending therethrough; and a distal surface comprising a light; a movable member extending longitudinally at least partially within the lumen, the movable member comprising a second lumen extending therethrough; and a camera extending longitudinally at least partially within the second lumen, the light received by a lens of the camera; wherein an illumination characteristic of the light is configured to be controlled by: proximal or distal movement of the movable member relative to the elongate tube along the longitudinal axis; rotational movement of the movable member about the longitudinal axis; or any combination of by proximal or distal movement of the movable member relative to the elongate tube along the longitudinal axis and rotational movement of the movable member about the longitudinal axis.

A second aspect relates to the scope system of aspect 1, wherein an outer surface of the movable member and/or an inner surface of the elongate tube comprises a conductive surface configured to provide an indication of proximal or distal and/or rotational movement of the movable member relative to the elongate tube.

A third aspect relates to the scope system of any preceding aspect, wherein an outer surface of the movable member and/or an inner surface of the elongate member comprises a visual marker configured to provide an indication of proximal, distal, and/or rotational movement of the movable member relative to the elongate tube.

A fourth aspect relates to the scope system of any preceding aspect, wherein an outer surface of the movable member and/or an inner surface of the elongate member comprises a protrusion, a depression, a keying feature, and/or a shape set curve configured to provide an indication of proximal, distal, and/or rotational movement of the movable member relative to the elongate tube.

A fifth aspect relates to the scope system of any preceding aspect, wherein each of a distal end of the movable member and/or the distal end of the elongate tube is configured for independent steering; wherein a proximal end of the scope system comprises switchable steering controls; and wherein the illumination characteristic of the light is controllable by switching the switchable steering controls.

A sixth aspect relates to the scope system of any preceding aspect, wherein the elongate tube and/or the movable member comprises a motion sensor configured to detect an indication of proximal or distal and/or rotational movement of the movable member relative to the elongate tube.

A seventh aspect relates to the scope system of any preceding aspect, wherein the elongate tube and/or the movable member comprises a photosensor configured to detect an indication of the illumination characteristic surrounding the distal surface.

An eighth aspect relates to the scope system of any preceding aspect, wherein the illumination characteristic of the light comprises an illumination level, an illumination color, an illumination frequency, gain, contrast, or exposure; and wherein the illumination characteristic is configured to be controlled by providing feedback from a motion sensor or a photosensor to a lighting control system.

A ninth aspect relates to the scope system of any preceding aspect, wherein the scope system is configured to provide a user with at least one of a haptic indication and a visual indication of the proximal or distal movement and/or the rotational movement of the movable member.

A tenth aspect relates to the scope system of any preceding aspect, wherein the scope system is configured for manual control of the illumination characteristic of the light.

An eleventh aspect relates to a scope system, comprising: an elongate tube comprising a lumen extending therethrough and a distal end section; an accessory channel movably disposed at least partially within the lumen of the elongate tube, the accessory channel comprising a second lumen extending therethrough; and a camera extending longitudinally at least partially within the second lumen, the camera comprising a lens; wherein a distal section of the accessory channel is rotatably movable about a pivot point between a forward-facing direction and an angled direction, the pivot point being fixed relative to the distal end section of the elongate tube; wherein a light is fixed to the distal section of the accessory channel such that when the distal section of the accessory channel rotates between the forward-facing direction and the angled direction, the light also rotates relative to the distal end section of the accessory channel, the light received by the lends; and wherein an illumination characteristic of the light is configured to be at least partially controlled by at least one of a proximal movement of the elongate tube, a distal movement of the elongate tube, and a rotational movement of the distal section about the pivot point between the forward-facing direction and the angled direction.

A twelfth aspect relates to the scope system of aspect 11, wherein each of the distal section of the accessory channel and the distal end section of the elongate tube is configured for independent steering; wherein a proximal end of the scope system comprises switchable steering controls; and wherein the light is configured to be controlled by switching the switchable steering controls.

A thirteenth aspect relates to the scope system of aspect 11 or 12, wherein the elongate tube and/or the accessory channel comprises a motion sensor configured to detect an indication of rotational movement of the distal section about the pivot point and/or proximal or distal movement of the distal end section.

A fourteenth aspect relates to the scope system of any one of aspects 11 to 13, wherein the distal end section and/or the distal section comprises a photosensor configured to detect an indication of the illumination characteristic surrounding the distal end section.

A fifteenth aspect relates to the scope system of any one of aspects 11 to 14, wherein the illumination characteristic of the light is configured to be controlled by providing feedback from a motion sensor or a photosensor to a lighting control system.

A sixteenth aspect relates to the scope system of any one of aspects 11 to 15, wherein the scope system is configured to provide a user with an indication of the proximal or distal movement of the distal end section and/or the rotational movement of the distal section of the accessory lumen about the pivot point.

A seventeenth aspect relates to the scope system of any one of aspects 11 to 16, wherein the scope system is configured for manual control of the illumination characteristic of the light.

An eighteenth aspect relates to a scope system, comprising: an elongate tube defining a longitudinal axis therethrough, the elongate tube comprising: a lumen extending therethrough; and a distal surface comprising a light; a movable member extending longitudinally at least partially within the lumen, the movable member comprising a second lumen extending therethrough; a photosensor on the elongate tube and/or the movable member configured to detect an indication of an illumination characteristic surrounding the distal surface and/or distal or proximal movement of the movable member relative to the elongate tube and/or rotational movement of the movable member about the longitudinal axis; and a detection circuit electronically connected to the photosensor, the detection circuit comprising a processor; wherein the processor is configured to cause: an increase in a level of the illumination characteristic when the photosensor detects an indication of an illumination characteristic that is lower than a predetermined minimum level of the illumination characteristic; and a decrease in a level of the illumination characteristic when the photosensor detects an indication of an illumination characteristic that is higher than a predetermined maximum level of the illumination characteristic.

A nineteenth aspect relates to the scope system of aspect 18, further comprising a camera extending longitudinally at least partially within the second lumen, the camera comprising the photosensor.

A twentieth aspect relates to the scope system of aspect 18 or 19, wherein the elongate tube and/or the movable member comprises a motion sensor configured to detect an indication of proximal, distal, or rotational movement of the movable member relative to the elongate tube.

In addition to the features mentioned in each of the independent aspects enumerated above, some examples may show, alone or in combination, the optional features mentioned in the dependent aspects and/or as disclosed in the description above and shown in the figures.

What is claimed is:

1. A scope system, comprising:
    an elongate tube defining a longitudinal axis therethrough, the elongate tube comprising:
        a lumen extending therethrough; and
        a distal surface comprising a light;
    a movable member extending longitudinally at least partially within the lumen, the movable member comprising a second lumen extending therethrough; and
    a camera extending longitudinally at least partially within the second lumen, the light received by a lens of the camera;
    wherein an illumination characteristic of the light is configured to be controlled by:
    proximal or distal movement of the movable member relative to the elongate tube along the longitudinal axis by:
    rotational movement of the movable member about the longitudinal axis; or
    any combination of by proximal or distal movement of the movable member relative to the elongate tube along the longitudinal axis and rotational movement of the movable member about the longitudinal axis.

2. The scope system of claim 1, wherein an outer surface of the movable member and/or an inner surface of the elongate tube comprises a conductive surface configured to provide an indication of proximal or distal and/or rotational movement of the movable member relative to the elongate tube.

3. The scope system of claim 1, wherein an outer surface of the movable member and/or an inner surface of the elongate tube comprises a visual marker configured to provide an indication of proximal, distal, and/or rotational movement of the movable member relative to the elongate tube.

4. The scope system of claim 1, wherein an outer surface of the movable member and/or an inner surface of the elongate tube comprises a protrusion, a depression, a keying feature, and/or a shape set curve configured to provide an indication of proximal, distal, and/or rotational movement of the movable member relative to the elongate tube.

5. The scope system of claim 1, wherein each of a distal end of the movable member and the distal end of the elongate tube is configured for independent steering;
    wherein a proximal end of the scope system comprises switchable steering controls; and
    wherein the illumination characteristic of the light is controllable by switching the switchable steering controls.

6. The scope system of claim 1, wherein the elongate tube and/or the movable member comprises a motion sensor configured to detect an indication of proximal or distal and/or rotational movement of the movable member relative to the elongate tube.

7. The scope system of claim 1, wherein the elongate tube and/or the movable member comprises a photosensor configured to detect an indication of the illumination characteristic surrounding the distal surface.

8. The scope system of claim 1, wherein the illumination characteristic of the light comprises an illumination level, an illumination color, an illumination frequency, gain, contrast, or exposure; and
    wherein the illumination characteristic is configured to be controlled by providing feedback from a motion sensor or a photosensor to a lighting control system.

9. The scope system of claim 1, wherein the scope system is configured to provide a user with at least one of a haptic indication and a visual indication of the proximal or distal movement and/or the rotational movement of the movable member.

10. The scope system of claim 1, wherein the scope system is configured for manual control of the illumination characteristic of the light.

11. The scope system of claim 1, wherein an illumination level of the light is configured to be adjusted upward or downward.

12. A scope system, comprising:
    an elongate tube comprising a lumen extending therethrough and a distal end section;
    an accessory channel movably disposed at least partially within the lumen of the elongate tube, the accessory channel comprising a second lumen extending therethrough; and
    a camera extending longitudinally at least partially within the second lumen, the camera comprising a lens;
    wherein a distal section of the accessory channel is rotatably moveable about a pivot point between a forward-facing direction and an angled direction, the pivot point being fixed relative to the distal end section of the elongate tube;
    wherein a light is fixed to the distal section of the accessory channel such that when the distal section of the accessory channel rotates between the forward-facing direction and the angled direction, the light also rotates relative to the distal end section of the accessory channel, the light received by the lens; and
    wherein an illumination characteristic of the light is configured to be at least partially controlled by at least a rotational movement of the distal section about the pivot point between the forward-facing direction and the angled direction.

13. The scope system of claim 12, wherein each of the distal section of the accessory channel and the distal end section of the elongate tube is configured for independent steering;

wherein a proximal end of the scope system comprises switchable steering controls; and wherein the light is configured to be controlled by switching the switchable steering controls.

14. The scope system of claim 12, wherein the elongate tube and/or the accessory channel comprises a motion sensor configured to detect an indication of rotational movement of the distal section about the pivot point and/or proximal or distal movement of the distal end section.

15. The scope system of claim 12, wherein the distal end section and/or the distal section comprises a photosensor configured to detect an indication of the illumination characteristic surrounding the distal end section.

16. The scope system of claim 12, wherein the illumination characteristic of the light is configured to be controlled by providing feedback from a motion sensor or a photosensor to a lighting control system.

17. The scope system of claim 12, wherein the scope system is configured for manual control of the illumination characteristic of the light.

18. A scope system, comprising:
an elongate tube defining a longitudinal axis therethrough, the elongate tube comprising:
a lumen extending therethrough; and
a distal surface comprising a light;
a movable member extending longitudinally at least partially within the lumen, the movable member comprising a second lumen extending therethrough; and
a photosensor on the elongate tube and/or the movable member configured to detect an indication of an illumination characteristic surrounding the distal surface and/or distal or proximal movement of the movable member relative to the elongate tube and/or rotational movement of the movable member about the longitudinal axis; and
a detection circuit electronically connected to the photosensor, the detection circuit comprising a processor;
wherein the processor is configured to cause:
an increase in a level of the illumination characteristic when the photosensor detects the indication of the illumination characteristic that is lower than a predetermined minimum level of the illumination characteristic; and
a decrease in a level of the illumination characteristic when the photosensor detects the indication of the illumination characteristic that is higher than a predetermined maximum level of the illumination characteristic.

19. The scope system of claim 18, further comprising a camera extending longitudinally at least partially within the second lumen, the camera comprising the photosensor.

20. The scope system of claim 18, wherein the elongate tube and/or the movable member comprises a motion sensor configured to detect an indication of proximal, distal, or rotational movement of the movable member relative to the elongate tube.

* * * * *